United States Patent
Adams et al.

(10) Patent No.: US 9,278,175 B2
(45) Date of Patent: Mar. 8, 2016

(54) DEVICE AND METHOD FOR TREATING DIVERTICULAR DISEASE

(71) Applicant: Empire Technology Development LLC, Wilmington, DE (US)

(72) Inventors: John Adams, Snohomish, WA (US); Daniel Hawkins, Bellevue, WA (US)

(73) Assignee: Empire Technologies Development LLC, Wilmington, DE (US)

( * ) Notice: Subject to any disclaimer, the term of this patent is extended or adjusted under 35 U.S.C. 154(b) by 177 days.

(21) Appl. No.: 14/009,279

(22) PCT Filed: May 8, 2013

(86) PCT No.: PCT/US2013/040069
§ 371 (c)(1),
(2) Date: Oct. 1, 2013

(87) PCT Pub. No.: WO2013/169852
PCT Pub. Date: Nov. 14, 2013

(65) Prior Publication Data
US 2014/0187858 A1    Jul. 3, 2014

Related U.S. Application Data

(60) Provisional application No. 61/645,372, filed on May 10, 2012.

(51) Int. Cl.
| A61M 5/158 | (2006.01) |
| A61B 17/00 | (2006.01) |
| A61B 17/12 | (2006.01) |
| A61B 17/34 | (2006.01) |
| A61B 1/018 | (2006.01) |
| A61M 25/00 | (2006.01) |

(52) U.S. Cl.
CPC ............. *A61M 5/158* (2013.01); *A61B 1/018* (2013.01); *A61B 17/00234* (2013.01);
(Continued)

(58) Field of Classification Search
CPC .................. A61B 17/00234; A61B 17/0057; A61B 17/12186; A61B 17/12195; A61B 17/3478; A61B 2017/00818; A61B 2017/00659; A61B 2017/00893; A61B 2017/00942; A61M 5/158; A61M 2025/0089
USPC ........... 604/506; 128/898; 606/190–192, 139, 606/144
See application file for complete search history.

(56) References Cited

U.S. PATENT DOCUMENTS

| 5,536,242 A | 7/1996 | Willard et al. | |
| 2005/0149099 A1* | 7/2005 | Yamano et al. | ................ 606/192 |

(Continued)

FOREIGN PATENT DOCUMENTS

| EP | 0 925 031 | 9/2003 |
| WO | WO 02/089655 | 11/2002 |

OTHER PUBLICATIONS

International Search Report and Written Opinion issued in PCT/US2013/040069, dated Jul. 24, 2013, in 12 pages.

*Primary Examiner* — Theodore Stigell
*Assistant Examiner* — Amber Stiles
(74) *Attorney, Agent, or Firm* — Knobbe Martens Olson & Bear, LLP

(57) ABSTRACT

Disclosed herein are methods and devices for treating diverticular disease. The method can include injecting a sterile fluid between a mucosal layer of the diverticulum and a serosal layer of the diverticulum to form an expanded cavity in the diverticulum comprising the sterile fluid; injecting a filler material in the expanded cavity; and removing at least a portion of the sterile fluid from the expanded cavity. The device can include a flexible overtube having a lumen; a flexible shaft at least partially disposed within the lumen of the flexible overtube; a cutting tip at a distal end of the flexible shaft; an input port fluidly coupled to the lumen of the flexible shaft; and an output port fluidly coupled to a proximal end of the lumen of the overtube. Also disclosed herein are systems and kits for treating diverticular disease.

20 Claims, 13 Drawing Sheets

(52) U.S. Cl.
CPC ...... *A61B 17/12186* (2013.01); *A61B 17/3478* (2013.01); *A61B 2017/00818* (2013.01); *A61M 2025/0089* (2013.01)

(56) References Cited

U.S. PATENT DOCUMENTS

| | | | |
|---|---|---|---|
| 2006/0070631 A1* | 4/2006 | Scopton | A61K 47/10 128/898 |
| 2010/0174306 A1* | 7/2010 | Mitelberg | A61B 17/32056 606/185 |
| 2011/0060358 A1 | 3/2011 | Stokes et al. | |
| 2011/0277777 A1* | 11/2011 | Alexander | A61B 17/12031 128/898 |
| 2011/0277778 A1 | 11/2011 | Alexander et al. | |
| 2011/0313343 A1 | 12/2011 | Milutinovic et al. | |

* cited by examiner

DEVICE AND METHOD FOR TREATING DIVERTICULAR DISEASE

CROSS-REFERENCE TO RELATED APPLICATIONS

This application is a United States national stage application under 35 U.S.C. §371 of PCT Application No. PCT/US2013/040069 designating the United States, filed on May 8, 2013, which claims priority benefit of U.S. Provisional Patent App. No. 61/645,372, filed on May 10, 2012, the contents of each of which are incorporated herein by reference in their entirety.

BACKGROUND

An outpouching of the colon or other body lumen, called a diverticulum, can become the site for inflammation known as diverticulitis, microperforation and/or bleeding. Current treatments may involve the surgical removal of segments of the body lumen. For extreme cases of diverticulitis, treatment can involve colon resection and placement of a colostomy. This approach results in significant healthcare costs and substantial pain for patients.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

A method for treating a diverticulum formed in a body lumen. The method can include: injecting a sterile fluid between a mucosal layer of the diverticulum and a serosal layer of the diverticulum to form an expanded cavity in the diverticulum containing the sterile fluid; injecting a filler material in the expanded cavity; and removing at least a portion of the sterile fluid from the expanded cavity.

A needle for treating a diverticulum formed in a body lumen. The needle can include: a flexible overtube having a lumen; a flexible shaft at least partially disposed within the lumen of the flexible overtube; a cutting tip at a distal end of the flexible shaft, the cutting tip having an opening fluidly coupled to the lumen of the flexible shaft; an input port fluidly coupled to the opening of the cutting tip; and an output port fluidly coupled to a proximal end of the lumen of the overtube. The flexible shaft can be configured to adjustably extend from a distal end of the flexible overtube.

A kit for treating a diverticulum formed in a body lumen. The kit can include: a flexible tubular assembly, a light source, a lens, and a needle. The flexible tubular assembly can be configured to be advanced in a body lumen. The light source can be configured to be at least partially disposed within a first lumen of the flexible tubular assembly. The lens can be configured to be at least partially disposed within a second lumen of the flexible tubular assembly. The needle can be configured to be at least partially disposed within a third lumen of the flexible tubular assembly. The needle can include: a flexible overtube having a lumen; a flexible shaft at least partially disposed within the lumen of the flexible overtube; a cutting tip at a distal end of the flexible shaft; an input port; and an output port. The flexible shaft can be configured to adjustably extend from a distal end of the flexible overtube. The cutting tip can include an opening fluidly coupled to the lumen of the flexible shaft. The input port can be fluidly coupled to the opening of the cutting tip. The output port can be fluidly coupled to a distal end of the lumen of the overtube.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1:
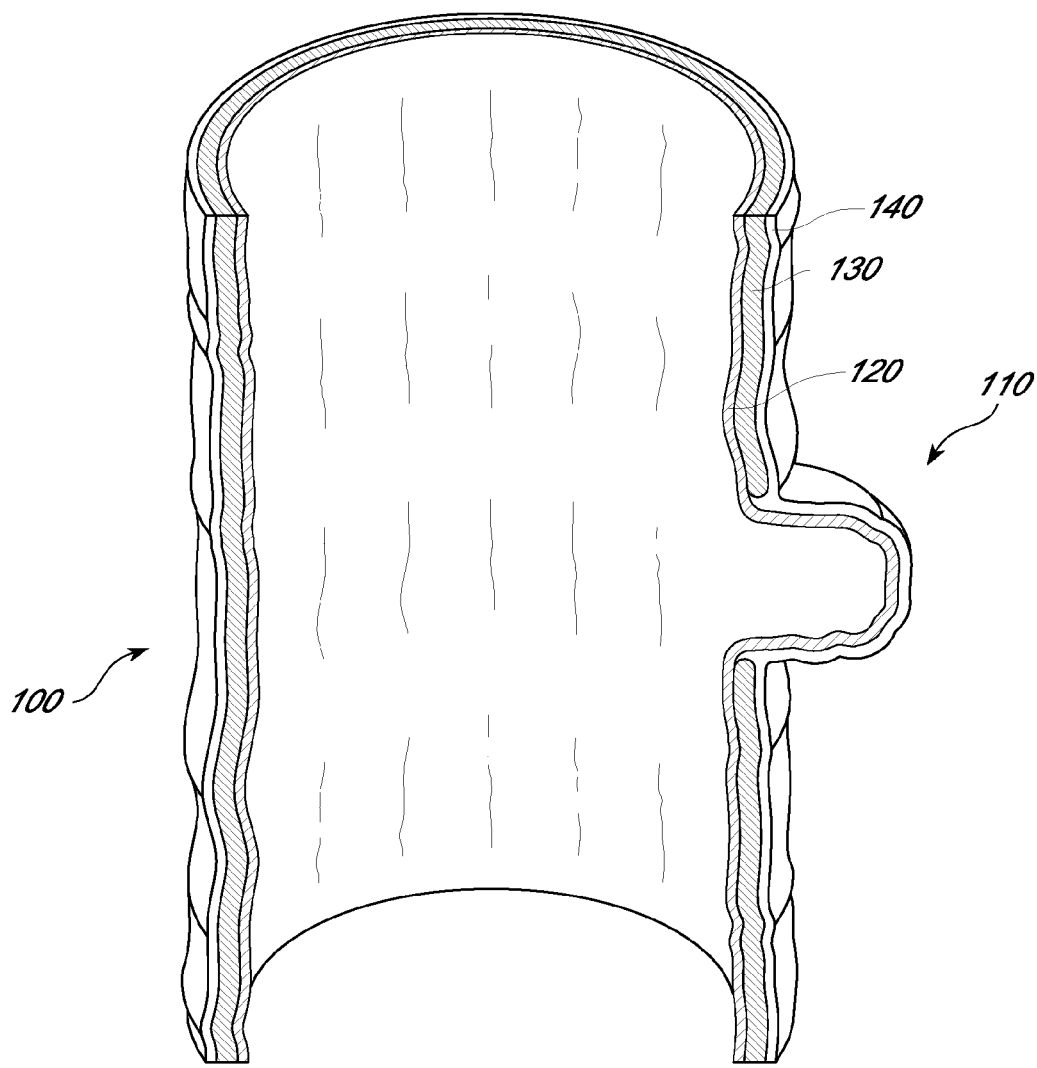
FIG. 1 is a sectional view of a diverticulum of the sigmoid colon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Disclosed herein are methods and devices for treating diverticular disease. The method can include injecting a sterile fluid between a mucosal layer of the diverticulum and a serosal layer of the diverticulum to form an expanded cavity in the diverticulum comprising the sterile fluid; injecting a filler material in the expanded cavity; and removing at least a portion of the sterile fluid from the expanded cavity. The device can include a flexible overtube having a lumen; a flexible shaft at least partially disposed within the lumen of the flexible overtube; a cutting tip at a distal end of the flexible shaft; an input port fluidly coupled to the lumen of the flexible shaft; and an output port fluidly coupled to a proximal end of the lumen of the overtube. Also disclosed herein are systems and kits for treating diverticular disease.

FIG. 1 is a sectional view of a diverticulum of the sigmoid colon. Sigmoid colon 100 includes mucosal layer 120, muscular layer 130, and serosal layer 140. Diverticulum 110 is one example of a diverticulum that can be treated using the devices and methods disclosed in the present application. Diverticulum 110 is located at gap in muscular layer 130 and includes mucosal 120 and serosal layer 140. The depth of a diverticulum is typically about 1-2 cm.

Figure 2:
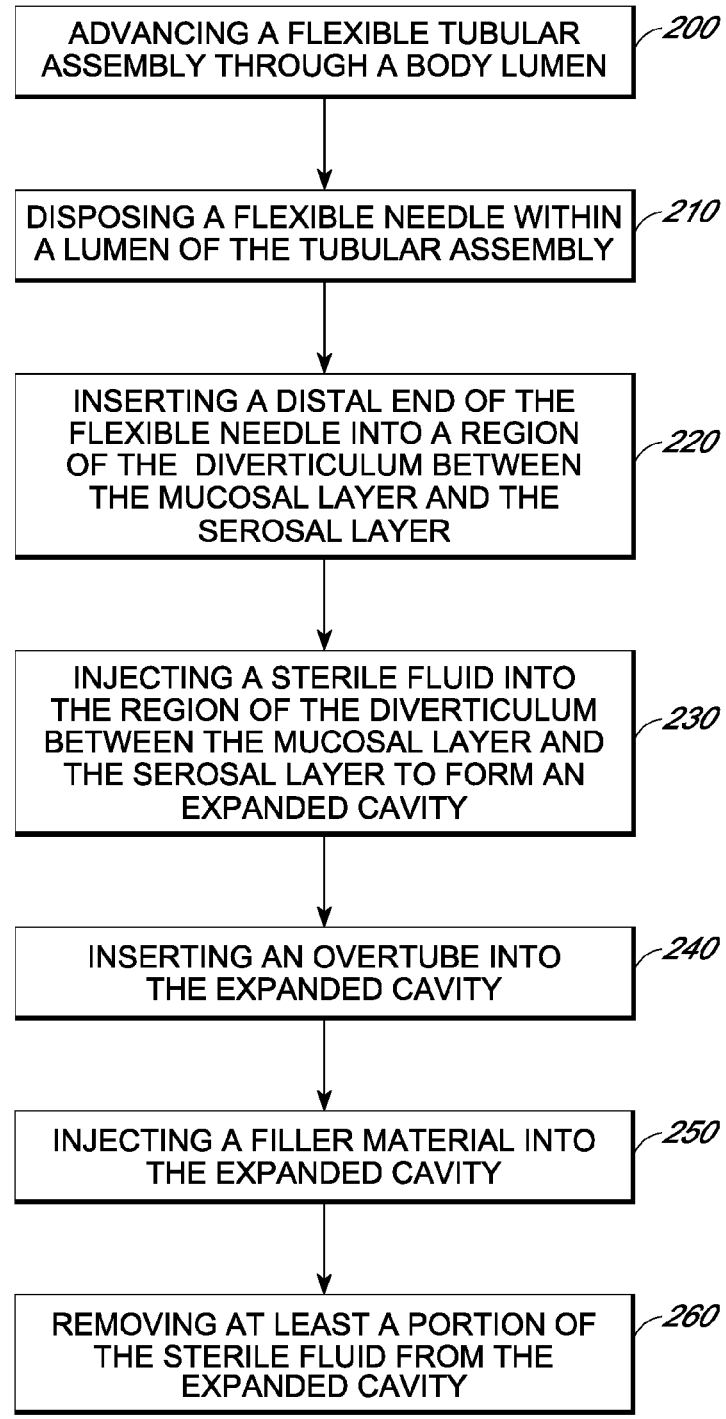
FIG. 2 is a flow diagram showing one example of a method for treating a diverticular disease within the scope of the present application.

FIG. 2 is a flow diagram showing one example of a method for treating a diverticular disease within the scope of the present application. The method of treating diverticular disease can include: "Advancing a flexible tubular assembly through a body lumen," illustrated in block 200; "Disposing a flexible needle within a lumen of the tubular assembly," illustrated in block 210; "Inserting a distal end of the flexible needle into a region of the diverticulum between the mucosal layer and the serosal layer," illustrated in block 220; "Injecting a sterile fluid into the region of the diverticulum between the mucosal layer and the serosal layer to form an expanded cavity," illustrated in block 230; "Inserting an overtube into the expanded cavity," illustrated in block 240; "Injecting a filler material into the expanded cavity," illustrated at block 250; and "Removing at least a portion of the sterile fluid from the expanded cavity," illustrated in block 260. Although operations 210-260 may be performed sequentially, it will be appreciated that one or more of these operations may be performed at about the same time. These operations may also be performed in a different order than is depicted in FIG. 2.

Figure 3:
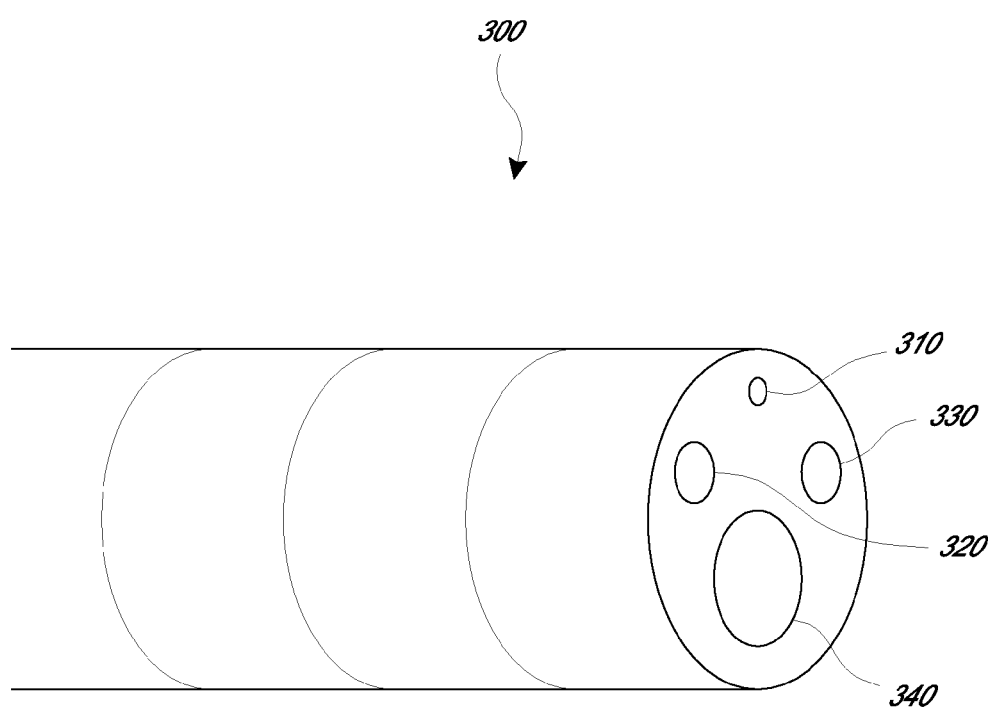
FIG. 3 is a view of a working end of a colonoscope that can be advanced through the intestine of a subject.

At operation 200 "Advancing a flexible tubular assembly through a body lumen," a flexible tubular assembly can be moved through a body lumen to a location near a diverticulum in the body lumen. FIG. 3 is a view of a working end of a colonoscope that can be advanced through the intestine of a subject. Colonoscope 300 is one example of a tubular assembly that can be used in the methods and devices for treating diverticular disease of the present application. Colonoscope 300 includes light source 310 configured to illuminate an area for viewing; viewing lens 320 configured to provide a user, such as a surgeon, with a field of vision; lumen 330 which can include a water source for flushing, a source of air, and/or a source of negative pressure; and working channel 340 through which tools such as biopsy forceps, graspers, or manipulators are typically passed. Colonoscopes are typically flexible and can be manipulated to bend and articulate along segments up to about 180 degrees. The dimensions of the colonoscope can vary, but may have a diameter from about 6 mm to about 20 mm and a length about 1 m to about 2 m. Working channel 340 can, for example, have a diameter of about 2 mm to about 5 mm.

Figure 4:
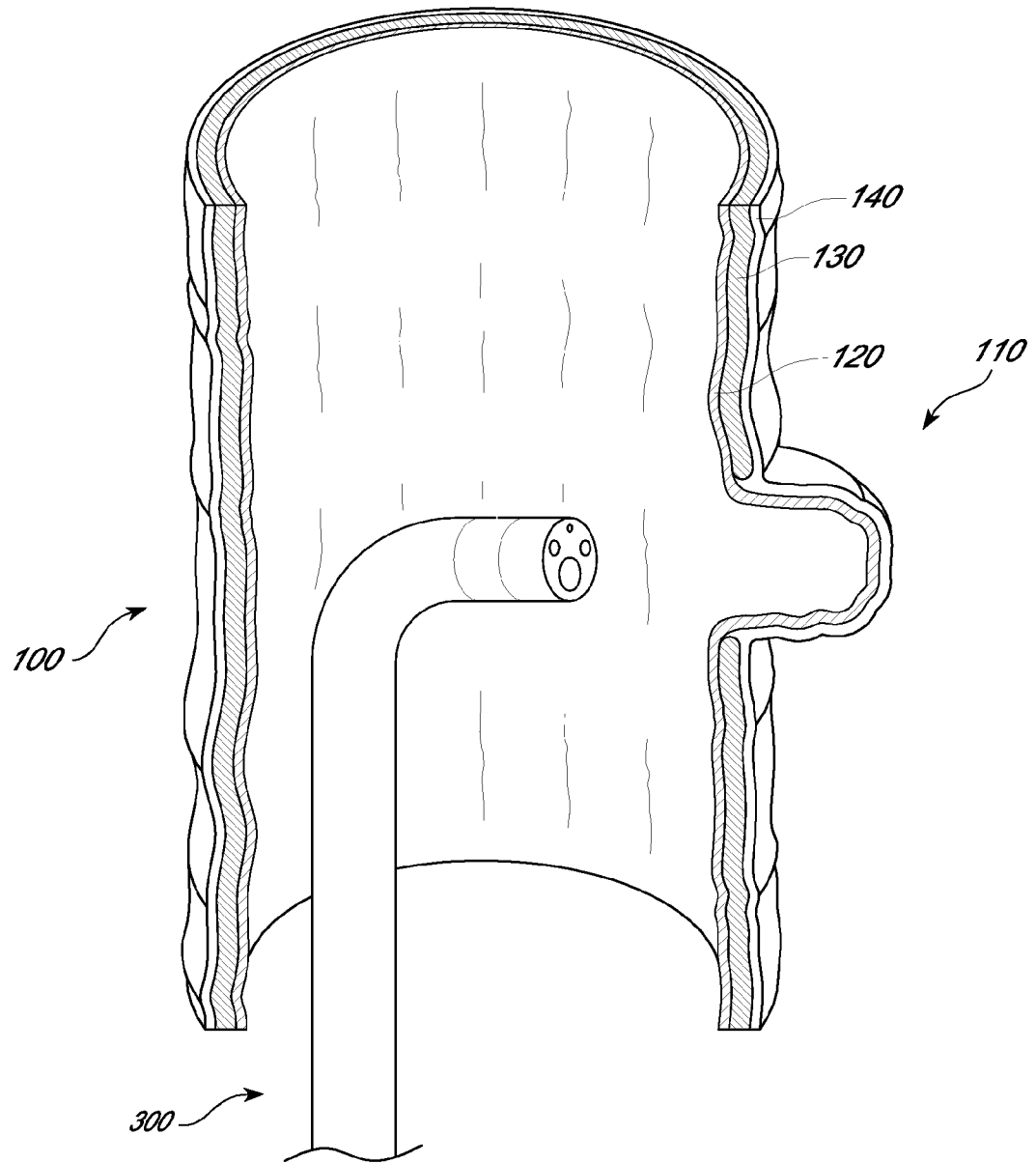
FIG. 4 is a side view of a colonoscope bent to view a diverticulum of the sigmoid colon.

The tubular assembly can be inserted into a body cavity or passageway, such as a colon, intestine, esophagus, etc. to treat the diverticular disease. As an example, the tubular assembly can be passed through the anus of a subject to reach the intestine. The intestine can be visually inspected (e.g., using light source 310 and viewing lens 320 on colonoscope 300) to identify one or more diverticula. FIG. 4 is a side view of a colonoscope bent to view a diverticulum of the sigmoid colon. Colonoscope 300 has suitable flexibility to bend about 90 degrees for viewing diverticulum 110.

Returning to FIG. 2, at operation 210 "Disposing a flexible needle within a lumen of the tubular assembly," a needle can be inserted into a lumen of the tubular assembly for accessing the diverticulum. As an example, after identifying a diverticulum in the colon using colonoscope 300, a needle can be at least partially disposed in working channel 340 of colonoscope 300 to access diverticulum 110. Alternatively, the needle may be disposed in working channel 340 of colonoscope 300 before advancing colonoscope 300 through sigmoid colon 100.

Figure 5:
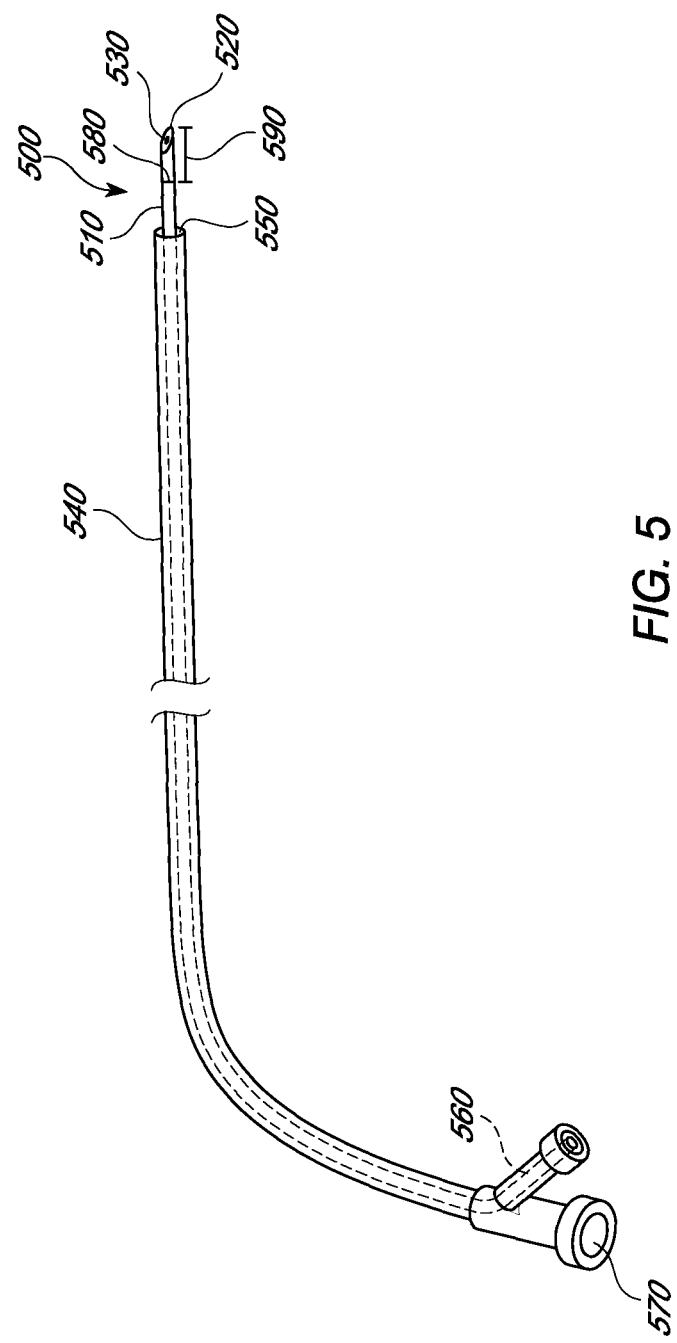
FIG. 5 is a perspective and partial sectional view of a needle configured to be disposed within the lumen of the tubular assembly.

FIG. 5 is a perspective and partial sectional view of a needle configured to be disposed within the lumen of the tubular assembly. Needle 500 includes sclerotherapy needle 510 having cutting tip 520 and opening 530 at a distal end. Sclerotherapy needle 510 is disposed within a lumen of overtube 540 and can be configured to adjustably extend from opening 550 at distal end of overtube 540 (e.g., sclerotherapy needle 510 can extend up to about 2 cm from opening 550). Needle 500 also includes input port 560 and output port 570. Input port 560 is fluidly coupled to opening 530 of sclerotherapy needle 510 and configured so that a fluid can be injected from input port 560. As an example, input port 560 can include a luer lock that couples to a syringe containing a fluid for injection. Output port 570 is fluidly coupled to opening 550 of overtube 540 so that a fluid can be withdrawn from opening 550 towards output port 570. For example, output port 570 can include a luer lock that couples to an empty syringe that can withdraw fluid by pulling the plunger on the syringe. The dimensions of the needle may vary so long as they can be disposed within the tubular assembly. As an example, needle 500 may be longer than colonoscope 300 and have a diameter less than the diameter of working channel 340 of colonoscope 300 (e.g., overtube 540 has a diameter of no more than about 3 mm). Needle 500 can have suitable flexibility for advancing through working channel 340 of colonoscope 300 while positioned in a body lumen.

Sclerotherapy needle 510 also includes marking 580 at fixed distance 590 from a distal end of sclerotherapy needle 510 (e.g., near cutting tip 520 and/or opening 530). Fixed distance 590 can be about the same as the depth of a region between the mucosal layer and the serosal layer of the diverticulum. For example, fixed distance 590 can be about 1 mm to about 3 mm. As discussed further below, a user may utilize marking 580 to determine when opening 530 has been disposed within the region between the mucosal layer and the serosal layer.

Returning to FIG. 2, at operation 220 "Inserting a distal end of the flexible needle into a region of the diverticulum between the mucosal layer and the serosal layer," the needle is inserted into the diverticulum so that a fluid can be injection between mucosal layer and serosal layer. As an example, cutting tip 520 of needle 500 can pierce through mucosal layer 120 at or near diverticulum 110 so that opening 530 of needle 500 is disposed between mucosal layer 120 and serosal layer 140. The needle can be guided into the appropriate region using standard endoscopic techniques. An appropriate depth for inserting needle 500 can optionally be determined by viewing the location of marking 580. For example, when marking 580 is at or near mucosal layer 120, this may indicate that opening 530 of needle 500 is at an appropriate location between the mucosal layer and the serosal layer.

Figure 6:
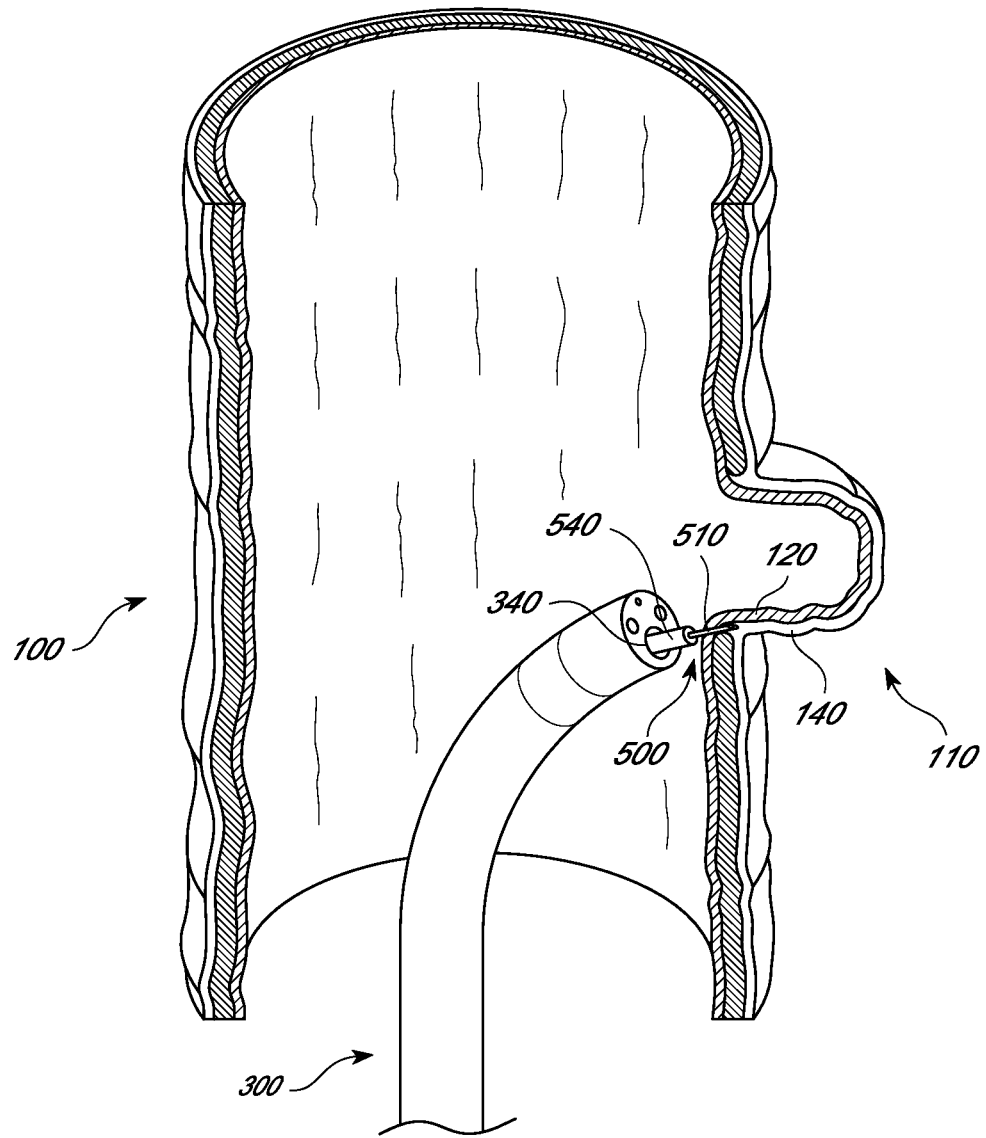
FIG. 6 is a side view of a needle inserted into a region of the diverticulum between the mucosal layer and the serosal layer.

FIG. 6 is a side view of a needle inserted into a region of the diverticulum between the mucosal layer and the serosal layer. Needle 500 extends from working channel 340 of colonoscope 300 through mucosal layer 120 of sigmoid colon 100. The distal end of overtube 540 and the distal end of sclerotherapy needle 510 can be on opposite sides of mucosal layer 120.

Returning again to FIG. 2, at operation 230 "Injecting a sterile fluid into the region of the diverticulum between the mucosal layer and the serosal layer to form an expanded cavity," a sterile fluid can be injected using the needle to form an expanded cavity. As an example, a syringe containing a sterile fluid can be coupled to input port 560 of needle 500 and the plunger of the needle can be depressed to displace the sterile fluid into the region of the diverticulum between the mucosal layer and the serosal layer. The sterile fluid can be saline or other isotonic, biocompatible liquids.

Figure 7:
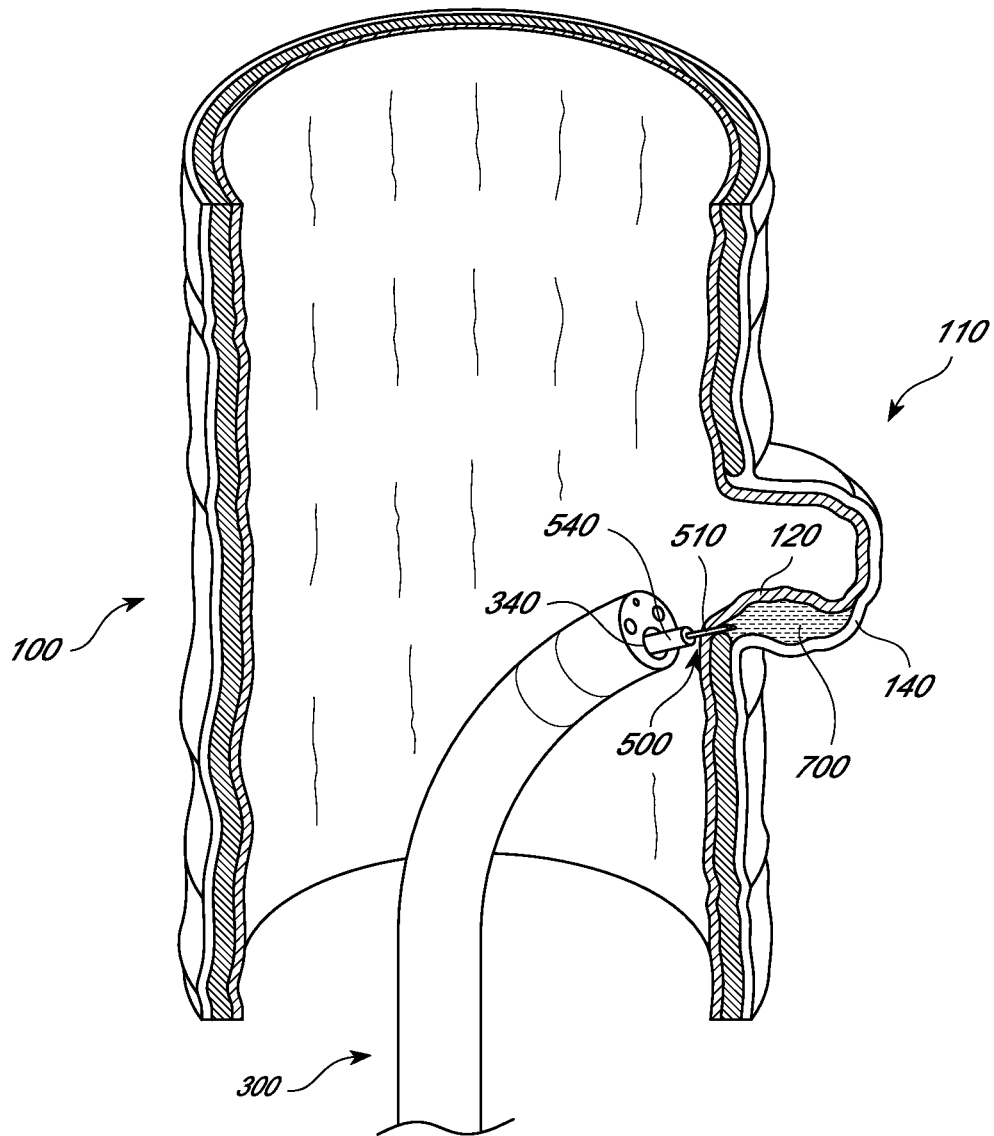
FIG. 7 is a side view of an expanded cavity initially formed in the diverticulum by injecting a sterile fluid.

FIG. 7 is a side view of an expanded cavity initially formed in the diverticulum by injecting a sterile fluid. While initially injecting sterile fluid 700, an expanded cavity forms between mucosal layer 120 and serosal layer 140 near the distal end of sclerotherapy needle 510. The pressure of sterile fluid 700 can spread apart mucosal layer 120 from serosal layer 140 at diverticulum 110 to form the expanded cavity.

During injection, a user may observe the site of injection to confirm that an expanded cavity is forming and, if needed, adjust the needle location or rate of injection accordingly. Furthermore, the pressure can optionally be monitored to reduce the likelihood of rupturing or tearing of the expanded cavity. As an example, if the fluid pressure increases above a pre-determined threshold, the rate of injection can be reduced. The pressure can be monitored using a suitable pressure sensor fluidly coupled to the needle. The fluid delivery and pressure can also be automated. For example, the fluid may be injected using a pump and monitored using a pressure sensor. Both the pump and pressure sensor can be coupled to a processor that is configured to adjust the rate of injection based, at least in part, on the measured pressure.

The volume of sterile fluid can also be monitored and the injection discontinued when a pre-determined volume is obtained. Also, as discussed further below, the total volume of sterile fluid injected may be measured and used to determine an appropriate volume of filler material to inject within the expanded cavity.

Figure 8:
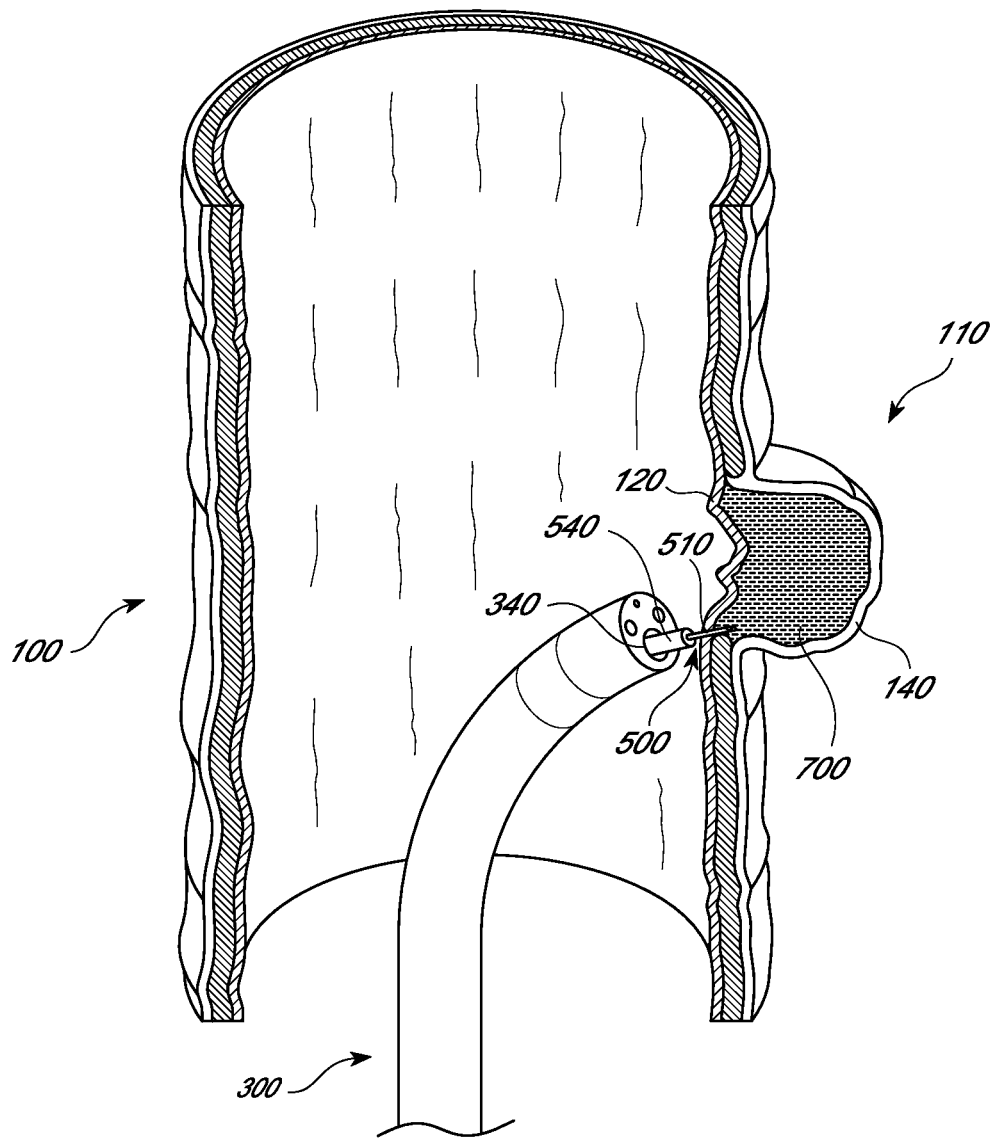
FIG. 8 is a side view of an expanded cavity that fills the diverticulum.

FIG. 8 is a side view of an expanded cavity that fills the diverticulum. After continued injection of sterile fluid 700, mucosal layer 120 and serosal layer 140 may be separated such that mucosal layer 120 is located near the inner wall of sigmoid colon 100. Injection of the sterile fluid can be discontinued when the mucosal layer reaches near the inner wall or a pre-determined volume of sterile fluid has been injected. The expanded cavity may have a volume that is about the same as the volume of the diverticulum before injecting the sterile fluid.

Figure 9:
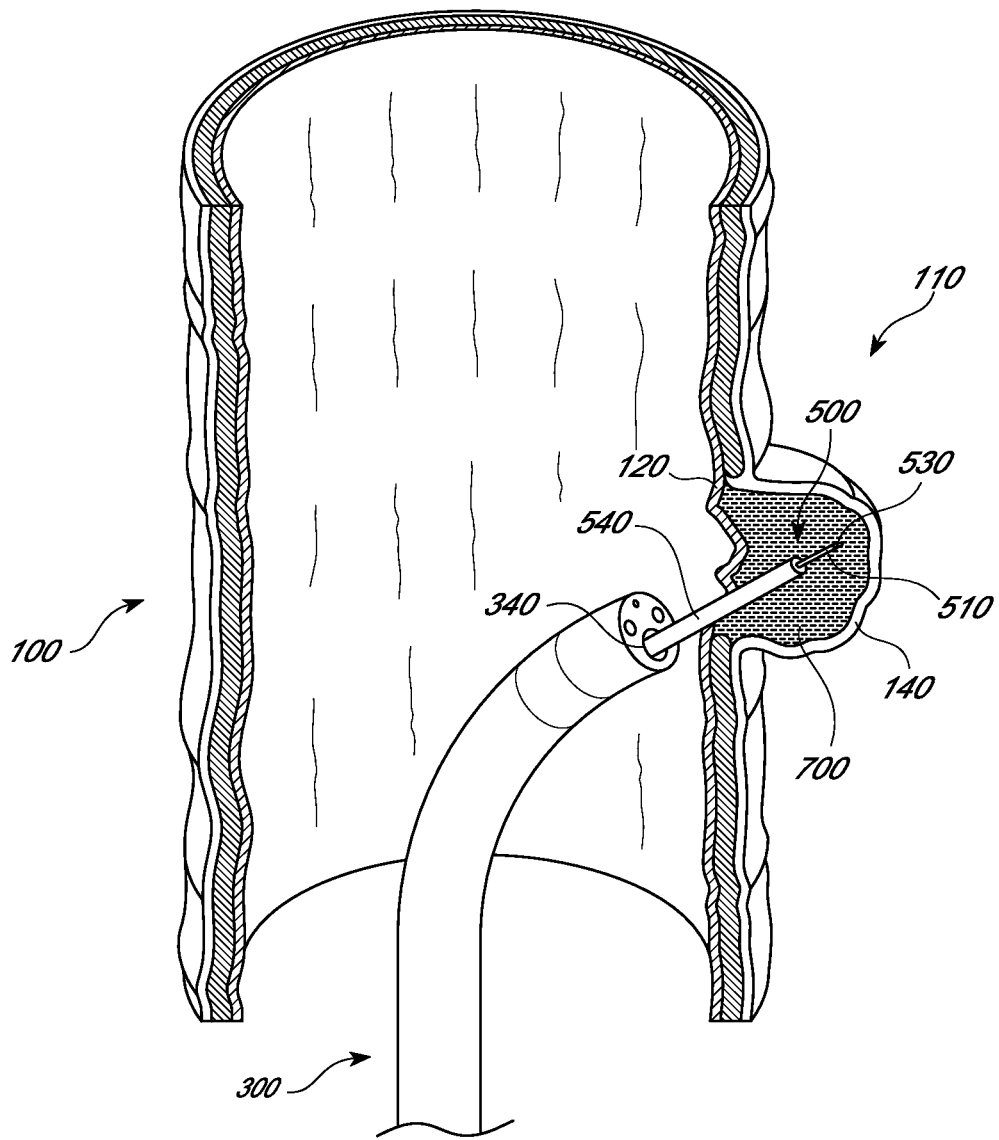
FIG. 9 is a side view of a needle having a distal end of an overtube inserted into the expanded cavity.

Returning to FIG. 2, at operation 240 "Inserting an overtube into the expanded cavity," an overtube can be inserted through the mucosal layer into the expanded cavity. For example, the distal end of the overtube can be advanced about 3-4 mm below the mucosal layer into the expanded cavity. FIG. 9 is a side view of a needle having a distal end of an overtube inserted into the expanded cavity. Overtube 540 has opening 550 disposed within the expanded cavity containing sterile fluid 700. Overtube 540 can be configured so that sterile fluid 700 can be removed from the expanded cavity via overtube 540 and received at output port 570. Sclerotherapy needle 510 can be extended from the distal end of overtube 540 in a direction from mucosal layer 120 toward serosal layer 140. For example, sclerotherapy needle 510 can be advanced about 8-10 mm further into the expanded cavity.

Figure 10:
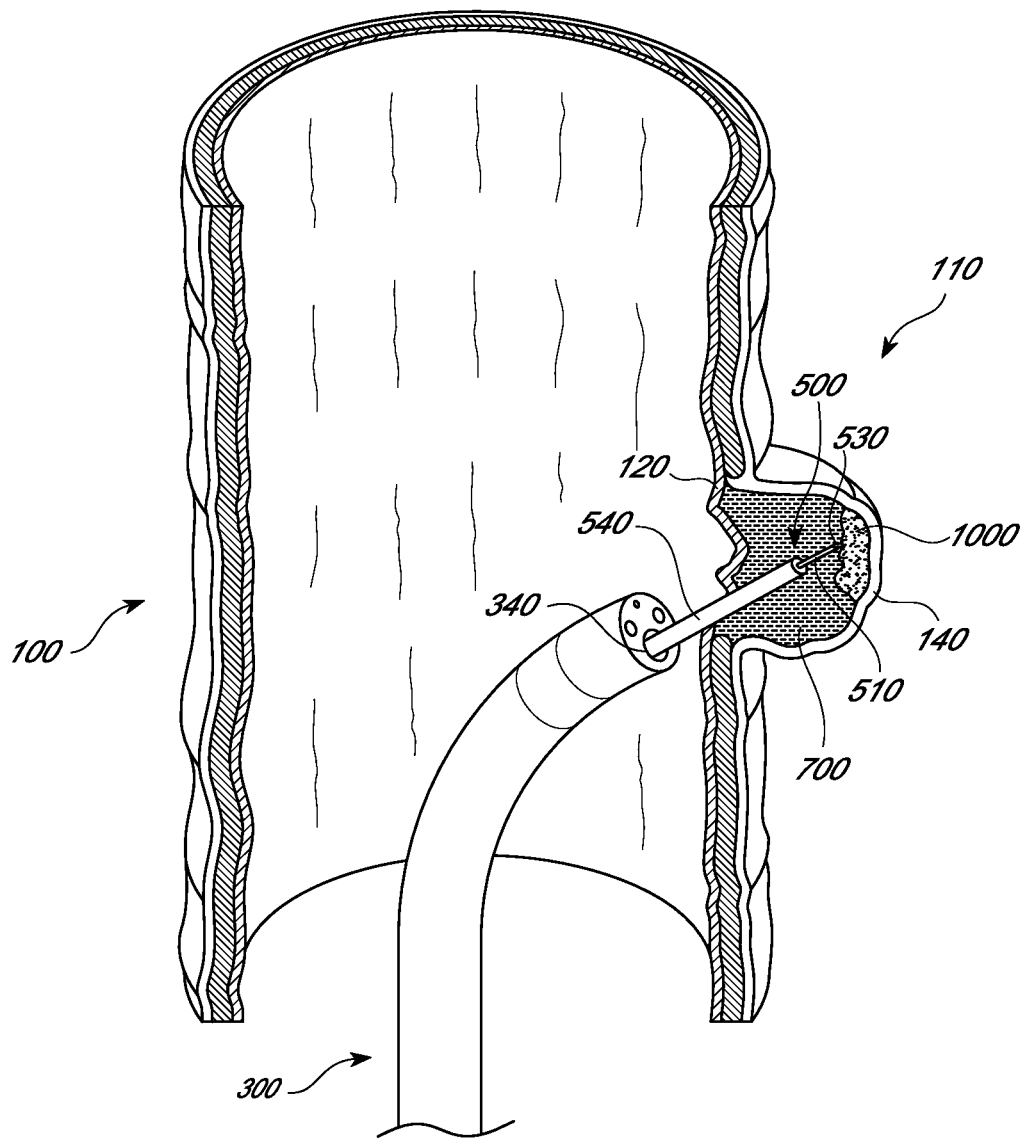
FIG. 10 is a side view of the expanded cavity after initially inserting a filler material.

Returning to FIG. 2, at operation 250 "Injecting a filler material into the expanded cavity," the expanded cavity is filled with an appropriate filler material using the needle. As an example, a syringe containing the filler material can be coupled to input port 560 of needle 500 and the plunger of the needle depressed to inject the filler material into the expanded cavity. FIG. 10 is a side view of the expanded cavity after initially inserting a filler material. Sclerotherapy needle 510 is extended so that filler material 1000 is initially placed near serosal layer 140 of the expanded cavity. Sterile fluid 700 can be disposed between filler material 1000 and mucosal layer 120.

Figure 11:
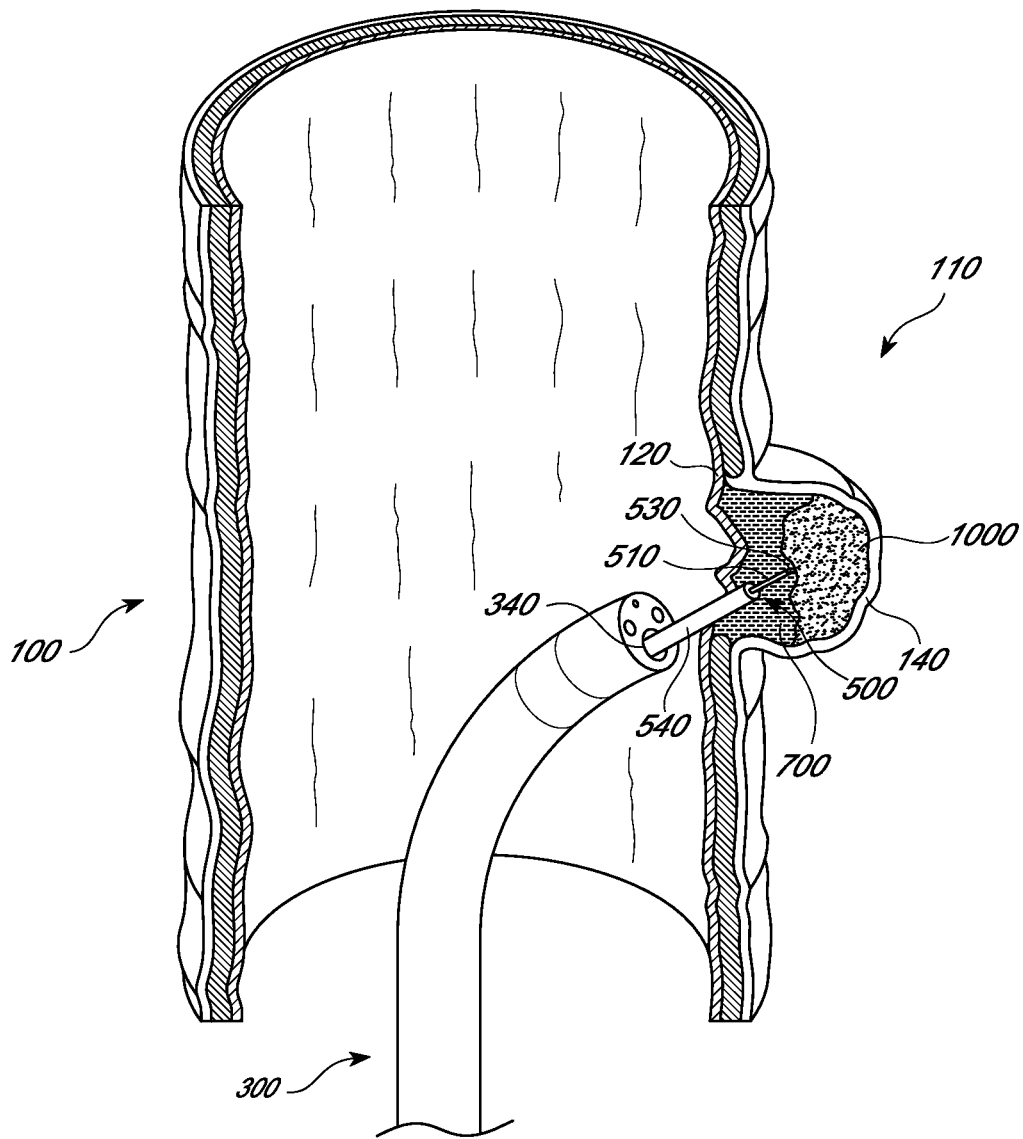
FIG. 11 is a side view of the expanded cavity after additional filler material is inserted.

FIG. 11 is a side view of the expanded cavity after additional filler material is inserted. As filler material 1000 is injected in the expanded cavity, the volume of filler material 1000 increases and the distance between filler material 1000 and mucosal layer 120 can decrease. Opening 530 of sclerotherapy needle 510 can be moved from serosal layer 140 to mucosal layer 120 (e.g., sclerotherapy needle 510 can be retracted into the lumen of overtube 540) as the volume of filler material 1000 in the expanded cavity increases. Moving opening 530 of sclerotherapy needle 510 towards mucosal layer 120 may reduce or prevent entrapping sterile fluid 700 between filler material 1000 and serosal layer 140.

Figure 12:
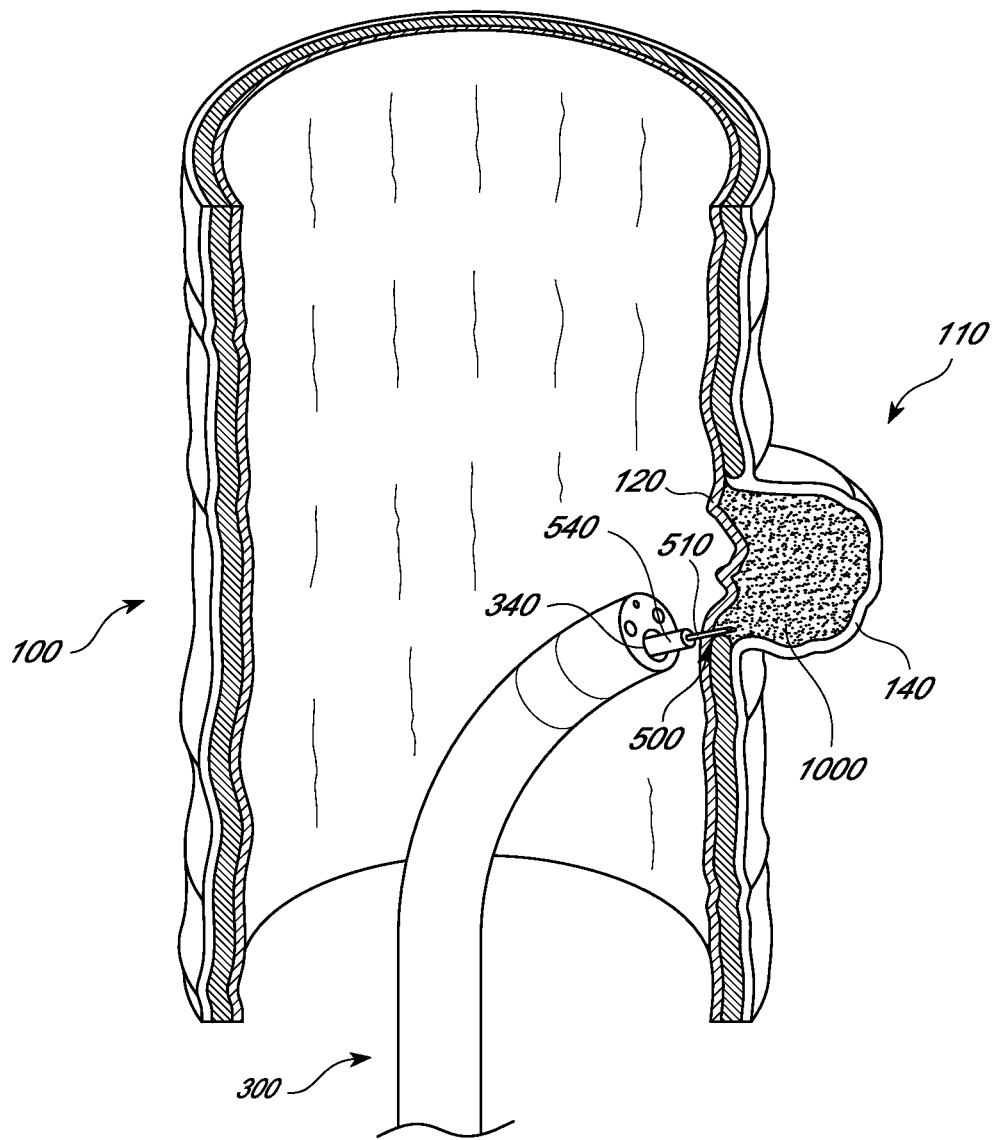
FIG. 12 is a side view of the expanded cavity filled with filler material.

FIG. 12 is a side view of the expanded cavity filled with filler material. The volume of expanded cavity can be about the same as the volume of filler material 1000. Sclerotherapy needle 510 can be disposed near mucosal layer 120 after the expanded cavity is filled with filler material 1000. The volume of filler material injected into the expanded cavity is not particularly limited. For example, the volume of filler material injected into the expanded cavity can be about the same as the volume of sterile fluid injected into the expanded cavity (e.g., the volume of filler material injected at operation 240 depicted in FIG. 2 is about the same as the volume of sterile fluid injected at operation 220 as depicted in FIG. 2). The volume of filler material injected can be determined by monitoring the volume of filler material in a syringe, or using a volumetric sensor fluidly coupled to input port 560 of needle 500. As another example, the volume of filler material injected into the expanded cavity can be determined by pressure measurements. A user may discontinue injecting the filler material when a measured pressure of the filler material obtains a pre-determined threshold. The pressure can be determined using, for example, a pressure sensor coupled to input port 560 of needle 500.

The filler material can be configured so that scar tissue forms in the expanded cavity. The filler material may include a polymer, a polysaccharide, hydrophilic colloids, sclerosing agents, microspheres, autologous cells, fibrous, organic, inorganic or a mixture thereof. Suitable fillers include synthetic polymers derived from vinyl, acrylate, methacrylate, urethane, ester and oxide monomers, naturally occurring polysaccharides such as chitin, chitosan, dextran and pullulan; gum agar, gum arabic, gum karaya, locust bean gum, gum tragacanth, carrageenans, gum ghatti, guar gum, xanthan gum and scleroglucan; starches such as dextrin and maltodextrin; hydrophilic colloids such as pectin; phosphatides such as lecithin; alginates such as ammonia alginate, sodium, potassium or calcium alginate, propylene glycol alginate; gelatin; collagen; and cellulosics such as ethyl cellulose (EC), methylethyl cellulose (MEC), Carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropylmethyl cellulose (HPMC), hydroxypropylmethyl cellulose phthalate (HPMCP), hydroxypropylmethyl cellulose acetate succinate (HPMCAS), hydroxypropylmethyl cellulose acetate trimellitate (HPMCAT), and ethylhydroxy ethylcellulose (EHEC). Other materials useful as the filler include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl)methacrylate chloride.

Returning to FIG. 2, at operation 260 "Removing at least a portion of the sterile fluid from the expanded cavity," the sterile fluid can be removed from the expanded so that filler material can be disposed in the expanded cavity. The sterile fluid can be removed before, during, or after injecting the filler material (e.g., operation 260 depicted in FIG. 2 can be performed before, after, and/or at about the same time as operation 250 depicted in FIG. 2). The sterile fluid can be removed through opening 550 of overtube 540 and received at output port 570. Output port 570 can optionally be coupled to a reservoir that receives the sterile fluid. The reservoir can include markings for determining a volume of sterile fluid received. Output port 570 can also optionally be coupled to a volumetric sensor for measuring a volume or weight of sterile fluid removed from the expanded cavity.

Figure 13:
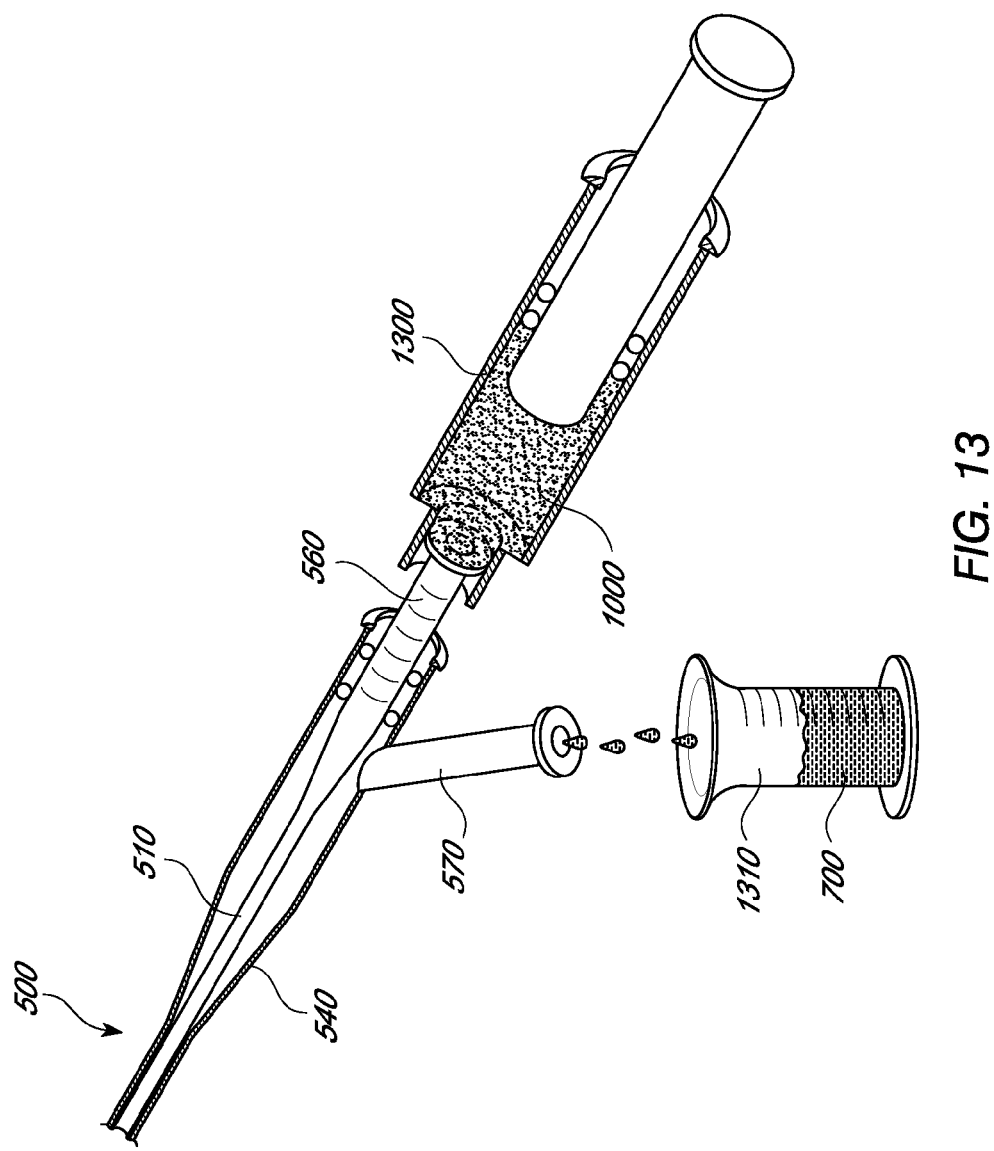
FIG. 13 shows the proximal end of a needle while removing sterile fluid from an expanded cavity.

FIG. 13 shows the proximal end of a needle while removing sterile fluid from an expanded cavity. Input port 560 of needle 500 is fluidly coupled to syringe 1300 containing filler material 1000. The plunger of syringe 1300 can be depressed to inject filler material into the expanded cavity via sclerotherapy needle 510. As filler material 1000 displaces into the expanded cavity (e.g., as depicted in FIGS. 9 and 10), sterile fluid 700 displaces from the expanded cavity into reservoir 1310 via overtube 540. A negative pressure can optionally be applied to overtube 540 using, for example, a vacuum fluidly coupled to output port 570 to aid withdrawal.

The volume of sterile fluid removed from the expanded cavity (e.g., sterile fluid 700 in reservoir 1310 depicted in FIG. 13) can be monitored. For example, when the volume of sterile fluid removed from the expanded cavity is about the same as the volume of sterile fluid injected into the expanded cavity (e.g., sterile fluid injected during operation 220 as depicted in FIG. 2), a user can discontinue injecting filler material into the expanded cavity. This procedure may be automated using volumetric sensors and/or pressure sensors that are coupled to input port 560 and/or output 570, and an appropriate pump (e.g., syringe pump or Harvard pump), each coupled to a processor configured automate injecting the filler material until a pre-determined threshold (e.g., pressure of filler material, volume of sterile fluid removed, or volume of filler material injected) is obtained.

After the expanded cavity has been filled with an appropriate amount of filler material, the needle can be removed from the expanded cavity. The hole in the mucosal layer formed by the needle can be optionally closed using sutures or an appropriate adhesive. The tubular assembly may then be used to search for additional diverticula. If one or more additional diverticula are present, the tubular assembly can be disposed near a second diverticulum and the treatment can be repeated (e.g., operations 200-260 as depicted in FIG. 2 are repeated on the second diverticulum). The repeated treatments can be completed without removing the tubular assembly from the intestine, and optionally, without removing the needle from the working channel.

While the description generally refers to colonoscopes and treatments within a colon, the devices and methods described herein are not limited to applications within a colon. They can be used to invert and/or treat outpocketings (e.g., diverticula, aneurisms, etc.) in any body lumen. Any reference to a colonoscope should be understood to be applicable to endoscopes generally, and similarly, any reference to a colon should be understood to be applicable to any body lumen.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLE EMBODIMENTS

1. A method for treating a diverticulum formed in a body lumen, the method comprising:
    injecting a sterile fluid between a mucosal layer of the diverticulum and a serosal layer of the diverticulum to form an expanded cavity in the diverticulum comprising the sterile fluid;
    injecting a filler material in the expanded cavity; and
    removing at least a portion of the sterile fluid from the expanded cavity.
2. The method of Embodiment 1, wherein a volume of the expanded cavity is about the same as a volume of the diverticulum.
3. The method of any one of Embodiments 1-2, wherein injecting the sterile fluid between the mucosal layer of the diverticulum and the serosal layer of the diverticulum comprises moving the mucosal layer of the diverticulum toward an interior region of the body lumen.
4. The method of any one of Embodiments 1-3, wherein the sterile fluid is isotonic.
5. The method of any one of Embodiments 1-4, wherein the sterile fluid comprises saline.
6. The method of any one of Embodiments 1-5, wherein the sterile fluid is injected through a needle inserted through the mucosal layer.
7. The method of any one of Embodiments 1-6, further comprising maintaining a pressure in the expanded cavity below a pre-determined pressure.
8. The method of any one of Embodiments 1-7, wherein the filler material comprises at least one of a polymer, a polysaccharide, hydrophilic colloids, sclerosing agents, microspheres, or autologous cells.
9. The method of any one of Embodiments 1-8, wherein the filler material is injected into the expanded cavity at about the same time that the sterile fluid is removed from the expanded cavity.
10. The method of any one of Embodiments 1-9, wherein a volume of the filler material injected into the expanded cavity is about the same as a volume of the sterile fluid injected into the expanded cavity.
11. The method of any one of Embodiments 1-10, further comprising inserting a distal end of a flexible needle into a region of the diverticulum between the mucosal layer of the diverticulum and the serosal layer of the diverticulum,
    wherein injecting the sterile fluid between the mucosal layer of the diverticulum and the serosal layer of the diverticulum comprises displacing the sterile fluid through the needle into the region of the diverticulum between the mucosal layer of the diverticulum and the serosal layer of the diverticulum.
12. The method of Embodiment 11, further comprising:
    advancing a flexible tubular assembly through the body lumen to dispose a distal end of the tubular assembly near the diverticulum; and
    disposing the flexible needle within a lumen of the tubular assembly, the flexible needle extending at least from a proximal end of the tubular assembly to a distal end of the tubular assembly.
13. The method of any one of Embodiments 11-12, wherein injecting a filler material in the expanded cavity comprises displacing the filler material through the flexible needle into the expanded cavity.
14. The method of any one of Embodiments 11-13, further comprising inserting an overtube into the expanded cavity, wherein the flexible needle is disposed within the overtube and adjustably extends from a distal end of the overtube, and
    wherein removing at least a portion of the sterile fluid from the expanded cavity comprises displacing the sterile fluid through the overtube to a proximal end of the overtube.
15. The method of any one of Embodiments 11-14, further comprising moving a distal end of the flexible needle deeper into the expanded cavity towards the serosal layer.
16. The method of any one of Embodiments 11-15, wherein the body lumen comprises an intestine.
17. A needle for treating a diverticulum formed in a body lumen, the needle comprising:
    a flexible overtube comprising a lumen;
    a flexible shaft at least partially disposed within the lumen of the flexible overtube, the flexible shaft configured to adjustably extend from a distal end of the flexible overtube;
    a cutting tip at a distal end of the flexible shaft, the cutting tip comprising an opening fluidly coupled to the lumen of the flexible shaft;
    an input port fluidly coupled to the opening of the cutting tip; and
    an output port fluidly coupled to a proximal end of the lumen of the overtube.
18. The needle of Embodiment 17, wherein the flexible overtube has a diameter of no more than about 3 mm.
19. The needle of any one of Embodiments 17-18, wherein the flexible shaft is configured to adjustably extend a distance of no more than about 2 cm from the distal end of the flexible overtube.
20. The needle of any one of Embodiments 17-19, wherein the flexible shaft further comprises a marking at a fixed distance from the opening of the cutting tip, wherein the fixed distance is from about 1 to about 3 mm.
21. The needle of any one of Embodiments 17-19, wherein the flexible shaft further comprises a marking at a fixed distance from the opening of the cutting tip, wherein the fixed distance is about the same as a depth of a region between a mucosal layer and a serosal layer of the diverticulum in the body lumen.
22. The needle of any one of Embodiments 17-20, wherein the input port comprises a fastener configured to fluidly couple with a fluid delivery device.

23. The needle of any one of Embodiments 17-22, wherein the input port comprises a fastener configured to fluidly couple with a pressure sensor.

24. The needle of any one of Embodiments 17-23, wherein the output port comprises a fastener configured to fluidly couple with a reservoir.

25. The needle of any one of Embodiments 17-24, wherein the distal end of the flexible overtube is configured to be inserted through a mucosal layer.

26. A system for treating a diverticulum formed in a body lumen, the system comprising:
   a flexible tubular assembly comprising a plurality of lumens, the flexible tubular assembly configured to advance through the body lumen;
   a light source at least partially disposed in a first lumen of the tubular assembly;
   a viewing lens at least partially disposed in a second lumen of the tubular assembly; and
   a needle at least partially disposed in a third lumen of the tubular assembly and configured to adjustably extend from a distal end of the tubular assembly, the needle comprising:
      a flexible overtube comprising a lumen;
      a flexible shaft at least partially disposed within the lumen of the flexible overtube, the flexible shaft configured to adjustably extend from a distal end of the flexible overtube;
      a cutting tip at a distal end of the flexible shaft, the cutting tip comprising an opening fluidly coupled to the lumen of the flexible shaft;
      an input port fluidly coupled to the opening of the cutting tip; and
      an output port fluidly coupled to a distal end of the lumen of the overtube.

27. The system of Embodiment 26, further comprising a syringe fluidly coupled to the input port of the needle.

28. The system of Embodiment 27, wherein the syringe contains a sterile fluid.

29. The system of Embodiment 27, wherein the syringe contains a filler material.

30. The system of any one of Embodiments 26-29, further comprising a pressure sensor fluidly coupled to the input port.

31. The system of any one of Embodiments 26-30, further comprising a pump fluidly coupled to the input port and configured to displace a fluid through the needle.

32. The system of Embodiment 31, further comprising a processor in communication with the pressure sensor and the pump, the processor configured to reduce a flow rate of the pump if the pressure sensor measures a pressure above a pre-determined value.

33. The system of any one of Embodiments 26-32, a volumetric sensor fluidly coupled to the input port and configured to measure an amount of fluid injected through the needle.

34. The system of any one of Embodiments 26-33, a volumetric sensor fluidly coupled to the output port and configured to measure an amount fluid received through the overtube.

35. The system of any one of Embodiments 26-34, wherein the flexible shaft is configured to adjustably extend a distance of no more than about 2 cm from the distal end of the flexible overtube.

36. The system of any one of Embodiments 26-35, wherein the flexible shaft further comprises a marking at a fixed distance from the opening of the cutting tip, wherein the fixed distance is from about 1 mm to about 3 mm.

37. The system of any one of Embodiments 26-36, further a comprising a reservoir fluidly coupled to the overtube.

38. A kit for treating a diverticulum formed in a body lumen, the kit comprising:
   a flexible tubular assembly configured to be advanced in a body lumen;
   a light source configured to be at least partially disposed within a first lumen of the flexible tubular assembly;
   a lens configured to be at least partially disposed within a second lumen of the flexible tubular assembly; and
   a needle configured to be at least partially disposed within a third lumen of the flexible tubular assembly, the needle comprising:
      a flexible overtube comprising a lumen;
      a flexible shaft at least partially disposed within the lumen of the flexible overtube, the flexible shaft configured to adjustably extend from a distal end of the flexible overtube;
      a cutting tip at a distal end of the flexible shaft, the cutting tip comprising an opening fluidly coupled to the lumen of the flexible shaft;
      an input port fluidly coupled to the opening of the cutting tip; and
      an output port fluidly coupled to a distal end of the lumen of the overtube.

39. The kit of Embodiment 38, further comprising a pressure sensor configured to be coupled with the input port of the needle.

40. The kit of any one of Embodiments 38-39, further comprising a first volumetric sensor configured to be coupled with the input port of the needle.

41. The kit of any one of Embodiments 38-40, further comprising a second volumetric sensor configured to be coupled with the output port of the needle.

42. The kit of any one of Embodiments 38-41, further comprising a syringe configured to be fluidly coupled to the input port.

43. The kit of any one of Embodiments 38-42, further comprising a sterile fluid configured to be injected between a mucosal layer of the diverticulum and a serosal layer of the diverticulum.

44. The kit of any one of Embodiments 38-43, further comprising a filler material configured to be injected between a mucosal layer of the diverticulum and a serosal layer of the diverticulum.

45. The kit of any one of Embodiments 38-44, wherein the flexible shaft further comprises a marking at a fixed distance from the opening of the cutting tip, wherein the fixed distance is from about 1 to about 3 mm.

What is claimed is:

1. A method for treating a diverticulum formed in a body lumen, the method comprising:
   injecting a sterile fluid between a mucosal layer of the diverticulum and a serosal layer of the diverticulum to form an expanded cavity in the diverticulum comprising the sterile fluid;
   injecting a filler material in the expanded cavity;
   inserting an overtube into the expanded cavity; and
   removing at least a portion of the sterile fluid from the expanded cavity, wherein removing at least a portion of the sterile fluid from the expanded cavity comprises displacing the sterile fluid through the overtube to a proximal end of the overtube.

2. The method of claim 1, wherein a volume of the expanded cavity is about the same as a volume of the diverticulum.

3. The method of claim 1, wherein injecting the sterile fluid between the mucosal layer of the diverticulum and the serosal layer of the diverticulum comprises moving the mucosal layer of the diverticulum toward an interior region of the body lumen.

4. The method of claim 1, wherein the sterile fluid is isotonic.

5. The method of claim 1, wherein the sterile fluid comprises saline.

6. The method of claim 1, wherein the sterile fluid is injected through a needle inserted through the mucosal layer.

7. The method of claim 1, further comprising maintaining a pressure in the expanded cavity below a pre-determined pressure.

8. The method of claim 1, wherein the filler material comprises at least one of a polymer, a polysaccharide, hydrophilic colloids, sclerosing agents, microspheres, or autologous cells.

9. The method of claim 1, wherein the filler material is injected into the expanded cavity at about the same time that the sterile fluid is removed from the expanded cavity.

10. The method of claim 1, wherein a volume of the filler material injected into the expanded cavity is about the same as a volume of the sterile fluid injected into the expanded cavity.

11. The method of claim 1, further comprising inserting a distal end of a flexible needle into a region of the diverticulum between the mucosal layer of the diverticulum and the serosal layer of the diverticulum,
wherein injecting the sterile fluid between the mucosal layer of the diverticulum and the serosal layer of the diverticulum comprises displacing the sterile fluid through the needle into the region of the diverticulum between the mucosal layer of the diverticulum and the serosal layer of the diverticulum.

12. The method of claim 11, further comprising:
advancing a flexible tubular assembly through the body lumen to dispose a distal end of the tubular assembly near the diverticulum; and
disposing the flexible needle within a lumen of the tubular assembly, the flexible needle extending at least from a proximal end of the tubular assembly to a distal end of the tubular assembly.

13. The method of claim 11, wherein injecting a filler material in the expanded cavity comprises displacing the filler material through the flexible needle into the expanded cavity.

14. The method of claim 11, wherein the flexible needle is disposed within the overtube and adjustably extends from a distal end of the overtube.

15. The method of claim 11, further comprising moving a distal end of the flexible needle deeper into the expanded cavity towards the serosal layer.

16. The method of claim 11, wherein the body lumen comprises an intestine.

17. The method of claim 1, wherein removing at least a portion of the sterile fluid is before injecting the filler material in the expanded cavity.

18. The method of claim 1, wherein removing at least a portion of the sterile fluid is after injecting the filler material in the expanded cavity.

19. The method of claim 1, wherein removing at least a portion of the sterile fluid is during injecting the filler material in the expanded cavity.

20. The method of claim 1, wherein removing at least a portion of the sterile fluid comprises displacing the sterile fluid into a reservoir coupled to the proximal end of the overtube.

* * * * *

UNITED STATES PATENT AND TRADEMARK OFFICE
CERTIFICATE OF CORRECTION

PATENT NO. : 9,278,175 B2
APPLICATION NO. : 14/009279
DATED : March 8, 2016
INVENTOR(S) : Adams et al.

Page 1 of 1

It is certified that error appears in the above-identified patent and that said Letters Patent is hereby corrected as shown below:

On the Title Page, in Column 1, in Item (73), under "Assignee", Lines 1-2, delete "Empire Technologies Development LLC," and insert -- Empire Technology Development LLC, --, therefor.

Signed and Sealed this
Fourteenth Day of June, 2016

Michelle K. Lee
*Director of the United States Patent and Trademark Office*